US00RE37107E

(19) United States
(12) Reissued Patent
Wells-Roth

(10) Patent Number: US RE37,107 E
(45) Date of Reissued Patent: Mar. 20, 2001

(54) DEVICE AND METHOD FOR THE SURGICAL ANASTOMASIS OF TUBULAR STRUCTURES

(75) Inventor: David Wells-Roth, Washington, DC (US)

(73) Assignee: Surgical Innovations LLC, Boston, MA (US)

(21) Appl. No.: 09/299,449

(22) Filed: Apr. 26, 1999

Related U.S. Patent Documents

Reissue of:
(64) Patent No.: 5,868,765
Issued: Feb. 9, 1999
Appl. No.: 09/095,537
Filed: Jun. 10, 1998

(51) Int. Cl.[7] ..... A61B 17/04
(52) U.S. Cl. ..... 606/155; 606/153
(58) Field of Search ..... 606/153–156

(56) References Cited

U.S. PATENT DOCUMENTS 3,683,926 * 8/1972 Suzuki ..... 606/153
4,214,586 * 7/1980 Mericle ..... 606/155
4,587,969 * 5/1986 Gillis ..... 606/156
5,037,428 * 8/1991 Picha et al. ..... 606/155

* cited by examiner

*Primary Examiner*—Gary Jackson
(74) *Attorney, Agent, or Firm*—Morse, Altman & Martin

(57) ABSTRACT

A device for assisting in anastomosis of tubular structures. The basic device has a generally cylindrical shape with a pair of insertion arms and a central depression that provides a space for the needle to move through within the tubular structures while simultaneously providing support so that the suture needle thrust does not collapse the tubular structure wall. The depression may be configured to guide the path of the needle. A bridge connects the arms and prevents the needle from inadvertently coming in contact with the wall opposite that of the wall being sutured. The method includes an initial suture to join the sutures, inserting the device into the openings of the two structures, placing sutures in the walls adjacent to the depression, optionally rotating the device so the depression is aligned with each suture as it is being placed, removing the device, and tightening the sutures to complete the anastomosis.

43 Claims, 4 Drawing Sheets

DEVICE AND METHOD FOR THE SURGICAL ANASTOMASIS OF TUBULAR STRUCTURES

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a device and method for surgically joining severed small tubular structures.

2. The Prior Art

It is presently possible to surgically join small tubular structures, for example, severed arteries smaller than 5.0 millimeters (mm) in size, and even less than 1.0 mm in size. However, considerable surgical dexterity is required. If reunification of a patent conduit with normal or nearly normal flow is to be achieved, great pains must be taken to insure gentle handling of delicate tissues, particularly avoiding unnecessary stretching, crushing, or piercing of the tissues. Such trauma increases the likelihood of thrombosis and/or structural failure.

Anastomosis of small tubular structures is preferably performed under a microscope to aid in visualization. In the case of end-to-end anastomosis, the severed vessels are gently clamped so as to interrupt flow and to make the ends available for suture. An initial suture is installed to connect the ends together at a single point. This initial suture is usually positioned at the anatomically deepest aspect of the anastomosis, a position which is generally referred to as the "back wall" or "posterior wall" of the anastomosis. Additional sutures are then placed to join additional points of the separated ends.

A number of factors contribute to the difficulty of performing this procedure:

(a) Loss of configuration. When tubular structures, such as blood vessels, are emptied of their pressurized contents (such as blood), the tubular lumen collapses and the tubular shape is lost. The ends of such severed, collapsed structures are difficult to visualize in their previously intact configuration or their preferably restored configuration. They are also difficult to grasp and manipulate in order to suture.

(b) Trauma from instrumentation. In placing sutures through the vessel wall, the suture needle is passed through the wall either from outside to in or from inside to out. To facilitate passing a suture needle inward towards the lumen, an instrument, such as a small forceps, is typically inserted into the lumen in order to provide counter pressure to the thrust of the suturing needle, as well as to attempt to separate the wall being sutured from the wall behind it. Alternatively, the surgeon may be required to grasp the full thickness of the wall being sutured with a forceps in order to position it so that it may be pierced by the suturing needle. This requirement for forceps to grasp and manipulate the dissociated structures introduces an unwanted element of tissue trauma.

(c) Inadvertent misplacement of sutures. With tubular shapes, especially those of small diameter, the opposite wall from the point being sutured might be inadvertently pierced or traversed in the line of the thrust of the suturing needle, especially in placing sutures through the vessel wall from outside to in, toward the lumen. This is especially so because of the lumen being collapsed. Not only might tissues of the opposing wall be traumatized, but the lumen may be inadvertently sutures shut. The conventional use of a forceps either to exert counter-pressure on the vessel wall for counter pressure for the suture needle thrust, or to grasp the wall, does not fully protect the opposite wall from inadvertently being caught in the suture or traumatized by the suture needle.

(d) Spasm of the vessel. Trauma to the vessel may cause it to spasm, adding a complicating factor in performing these procedures.

(e) Time for performance. The present methods of performing anastomoses are time consuming. Surgical risk, particularly anesthetic risk, is known to be increased with time.

(f) Operator fatigue. The intense concentration, effort and time required by the present methods contribute to frustration and fatigue.

SUMMARY OF THE INVENTION

An object of the present invention is to provide a device and method for surgically joining severed small tubular structures that minimizes the problems associated with methods of the prior art. It renders the process less technically demanding, decreases tissue trauma associated with grasping and manipulating tissues, diminishes the occurrence of inadvertent piercing trauma in the line of suture needle thrust, facilitates speed, and decreases operator fatigue.

The basic device of the present invention has a generally cylindrical shape that includes a pair of insertion arms and a central depression. The depression leaves a bridge connecting the arms. The arms have free extremities that are preferably convexly rounded or tapered for ease in inserting the device into the tubular structure. The arms are smooth, coated with a lubricant, and/or composed of a material that retains moisture for ease in insertion. The lengths and/or cross-sections may be the same or different between the two arms as may be needed for particular applications. The cross-section may be round, oval, or such other desired shape. The arms may be solid or may include an axial bore. The arms are preferably constructed of a relatively firm material that is biologically compatible.

The depression provides a space for the needle to move through within the tubular structures while simultaneously the edge of the depression provides support so that the needle thrust does not collapse the wall. The depression may be configured to guide the path of the suture needle.

The configuration of the depression generally determines the configuration of the bridge, with some possible variations. For example, the bridge may be straight or curved, depending upon the desired final shape of the anastomosis. It may have a different cross-section than that of the arms.

Along with connecting the arms, one purpose of the bridge is to prevent the needle from inadvertently coming in contact with the wall opposite that of the wall being sutured. Preferably, the bridge is composed of a material that is difficult for the needle to penetrate and that is relatively flexible so that the device can be more easily removed from the tubular structures when no longer needed.

Examples of suitable materials for the device include polypropylene, dacron polyester, nylon, Teflon and polytetra-fluoroethylene (PTFE). Where resorbtion might be desired, the polyglycolic materials Vicryl and Dexon are suitable. The present invention also contemplates that the colors of the device may be vary depending upon a particular application. Optionally, the material of the device is radioopaque, in whole or in part, for the purpose of locating the device radiologically. Optionally, the material of the device is magnetized, in whole or in part, for the purpose of locating the device if lost in the surgical field.

The present invention also contemplates that the device contain or be coated with additional materials to accomplish supplemental objectives, such as clot prevention, spasm prevention and infection prevention.

Optionally, the device includes a means for being inserted and removed and/or manually rotated while residing in the tubular structure. One such means includes a grasping ridge within the bridge and a grasping tool configured to the shape of the ridge. A second such means includes an axial concavity in each arm into which feet of a grasping tool are inserted.

In the method of the present invention, that of an anastomosis of tubular structures, the first step is to put an initial suture on the back wall of the anastomosis. Then the device is inserted into the openings of the two structures by either inserting the device completely into one structure and sliding back into the other until in the working position, or by folding the device at the bridge, inserting each arm into the openings of the tubular structures, and allowing the device to straighten out into the working position. In the working position, the depression straddles the openings of the tubular structures. Next, the needle pierces one wall adjacent to the depression. Optionally, the edge of the depression is designed to exert a counter pressure to the wall so that the thrust of the needle does not collapse the wall. The depression provides enough space for the needle to pass perpendicularly through the wall and the bridge prevents the needle from contacting the opposite wall. Sutures, of either the individual or continuous type, are placed where necessary. The device may be rotated so that each new suture is centered in the depression to provide maximum protection to the structures walls. After the sutures are placed, the device is either flexed at the bridge and removed or, if the sutures are loose enough, slid completely into one of the structures and back out through the sutures. Finally, the sutures are closed to complete the anastomosis.

While the example cited relates to end-to-end anastomoses, the same principles apply to end-to-end anastomoses as well. The same principles apply equally well to all types of tubular structures, for example, to vascular structures, to tubular structures of the biliary tree, urologic, and reproductive systems, and to the joining of synthetic grafts to tissues.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION

Figures 1, 2, 3, 4, 5, 6, 7, 8, 9:
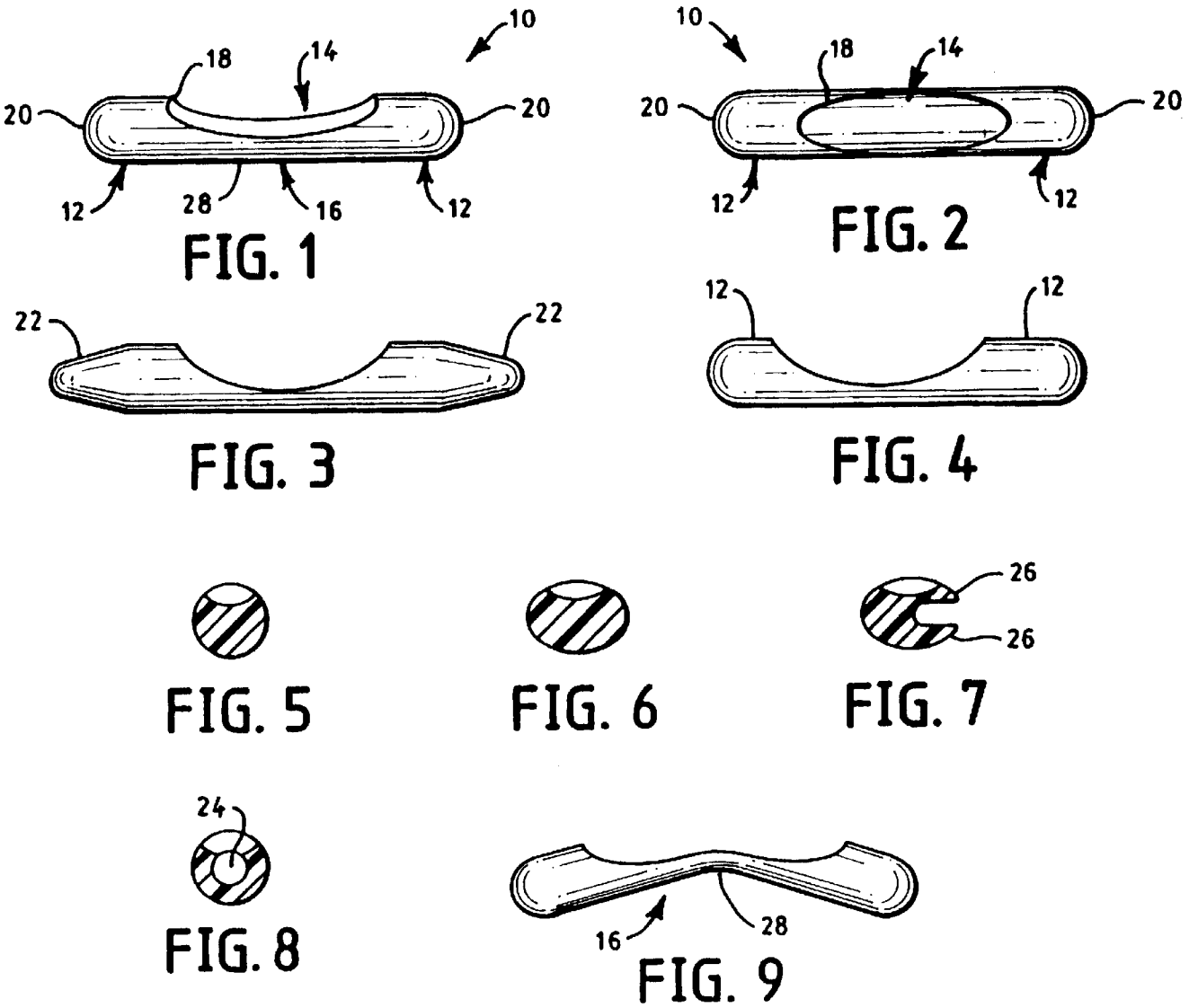
FIG. 1 is a side, perspective view of the basic embodiment of the device of the present invention.
FIG. 2 is a top view of the embodiment of FIG. 1.
FIG. 3 is a side view of device of the present invention with tapered extremities.
FIG. 4 is a side view of device of the present invention with arms of different lengths.
FIG. 5 is an end cross-sectional view of device of the present invention with a round cross-section.
FIG. 6 is an end cross-sectional view of device of the present invention with an oval cross-section.
FIG. 7 is an end cross-sectional view of device of the present invention with a compressible C-shaped cross-section.
FIG. 8 is an end view of device of the present invention with an axial bore.
FIG. 9 is a side view of device of the present invention with a curved bridge.

The basic embodiment 10 of the device of the present invention is illustrated in FIGS. 1 and 2. The basic device 10 has a generally cylindrical shape. The components of the basic device 10 include a pair of insertion arms 12 and a central depression 14. The depression 14 leaves a bridge 16 connecting the arms 12.

The insertion arms 12 are designed to be non-traumatic when in contact with the inside of the tubular structure. This is accomplished by either making the outer surface of the arms 12 smooth, by forming the arms 12 of a material that retains moisture, and/or by coating the arms 12 with a lubricant. As an aid to insertion, the free extremities 20 of the arms 12 are convexly rounded. Optionally, the free extremities are tapered, as at 22 in FIG. 3. A tapered extremity is easier to insert because the tubular structure, which is collapsed when empty, does not have to be opened as far to start the insertion process.

The arms 12 may have the same or different lengths, as in FIG. 4, and/or the same or different cross-sections, as in FIGS. 5–7, as may be needed for particular applications. The cross-sectional area is approximately that of the tubular structure so that it will support the structure without stretching it. The cross-section may be round, as in FIG. 5, oval, as in FIG. 6, or such other desired shape. For example, the C-shaped cross-section of FIG. 7 would allow narrowing by compressing the device at the edges 26 to facilitate insertion. The arms 12 may be solid or may include an axial bore 24, as in FIG. 8. The diameter of the bore 24 is determined by its function. If its function is merely to equalize pressures, the bore diameter can be minimized. The arms 12 are preferably constructed of relatively firm material. Preferably, the arms 12 are constructed of a biologically compatible material.

The depression 14 permits the suture needle room to move through the wall when passing from outside to inside, and allows space for the suture needle positioned inside the wall to be passed outwardly through the wall. The depth, length, and width of the depression 14 may vary depending upon the application. The depression 14 may be configured and positioned so that its edge 18 places counter pressure on the inside of the tubular structure wall so as to oppose the thrust of the suture needle when passed from outside to in. The depression 14 may be configured to guide the placing of sutures and/or limit the path of the suture needle.

The configuration of the bridge 16 is generally determined by the configuration of the depression 14. However, the detailed configuration may be designed for the particular size and anatomy of the structures to be joined. For example, the bottom surface 28 may be straight, as in FIG. 1, or curved, as in FIG. 9. It may have a different cross-section than that of the arms 12. It is preferable, but not essential, that the bridge 16 be composed of a material which allows the bridge 16 some flexibility for bending. Preferably, the arms 12 are not separable from the bridge 16, as one function of the bridge 16 is to pull the arms 12 from the tubular structure when suturing is complete.

A second function of the bridge 16 is to prevent needle contact with the wall of the tubular structure opposite that of the wall being sutured. In the process of suturing, when the suture needle passes into the depression 14, the bridge 16 prevents the needle from contact with the opposite wall. Accordingly, the bridge material, in addition to its preferred flexibility, is preferably made of a material and in a thickness which is difficult for the suture needle to penetrate.

Examples of materials suitable for the device of the present invention include, but are not limited to, polypropylene, dacron polyester, nylon, Teflon and polytetra-flouroethylene (PTFE), which are materials commonly used in surgery. Where resorbtion might be desired, it may be desirable that the device to be composed of a resorbable material, such as the polyglycolic material Vicryl and Dexon. The present invention contemplates that, depending upon application, the material of the device may be clear, opaque, or of a particular color or combination of colors, in whole or in part, to facilitate visualization. Optionally, the material of the device is radioopaque, in whole or in part, for the purpose of locating the device radiologically. Optionally, the material of the device is magnetized, in whole or in part, for the purpose of locating the device if lost in the surgical field.

The present invention also contemplates that it might be desirable for device to contain or be coated with additional materials to accomplish additional objectives. For example, the device might be coated with heparin to prevent clotting, with xylocaine or verapamil to prevent vascular spasm, and/or with an antibiotic or antiseptic to prevent infection.

Figure 11:
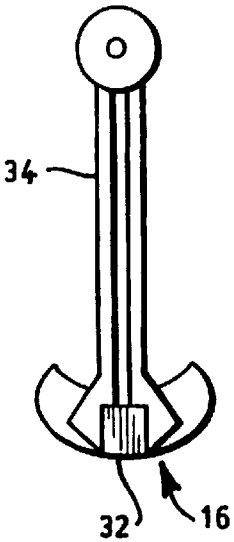
FIG. 11 is an end cross-sectional view of the configuration of FIG. 10.
Figure 10:
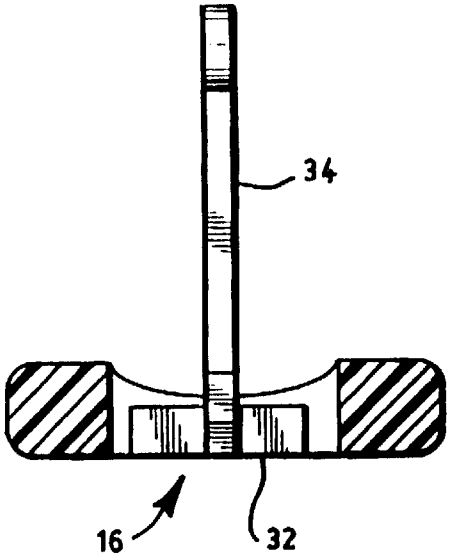
FIG. 10 is a side view of one configuration for manual rotation of the device.

Optionally, the device 10 includes a means for being inserted, removed and/or manually rotated while residing in the tubular structure. One such means is illustrated in FIGS. 10 and 11, and includes a grasping ridge 32 located within the bridge 16. The ridge 32 may be grasped with a grasping tool 34, particularly one congruously configured to the shape of the ridge 32. The tool 34 may be fitted with spring-like action, either as an independent spring or by virtue of the materials from which it is made. Such solutions for grasping devices are well known.

Figure 12:
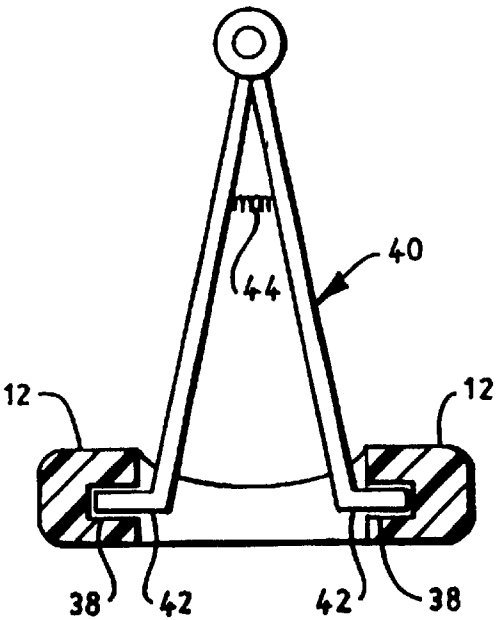
FIG. 12 is a side cross-sectional view of another configuration for manual rotation of the device.

A second inserting, removing and/or manually rotating means is illustrated in FIG. 12. Each arm 12 includes an axial concavity 38 which allows it to be held by a foot 42 of a grasping tool 40. When used for rotating the device 10, the concavities 38 and feet 42 may be keyed so that the tool 40 does not rotate within the concavities 38. Squeezing the tool 40 releases the device 10. Like above, the tool 40 may be fitted with spring-like action, either as an independent spring mechanism 44 or by virtue of the materials from which it is made. Again, such solutions for grasping devices are well known.

A third removal means includes a fixed tab that extends from the device, preferably through the space between the tubular structures. The device is removed by pulling the tab through the sutures.

Figure 13:
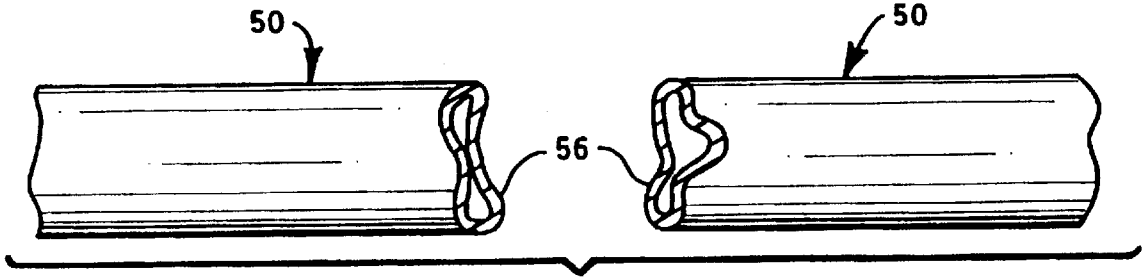
FIG. 13 shows the first step of an end-to-end anastomosis of the method of the present invention.
Figure 14:
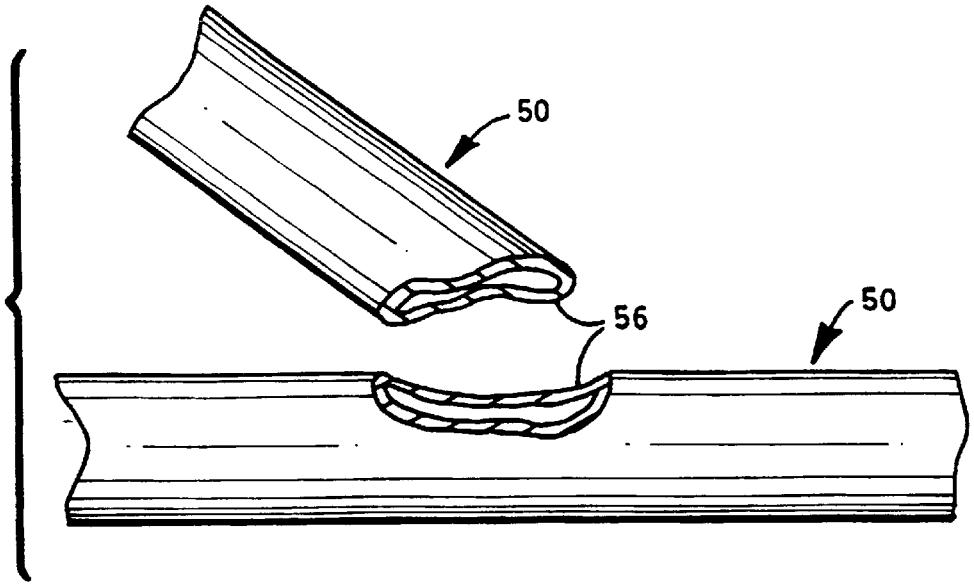
FIG. 14 shows the first step of an end-to-side anastomosis of the method of the present invention.
Figure 15:
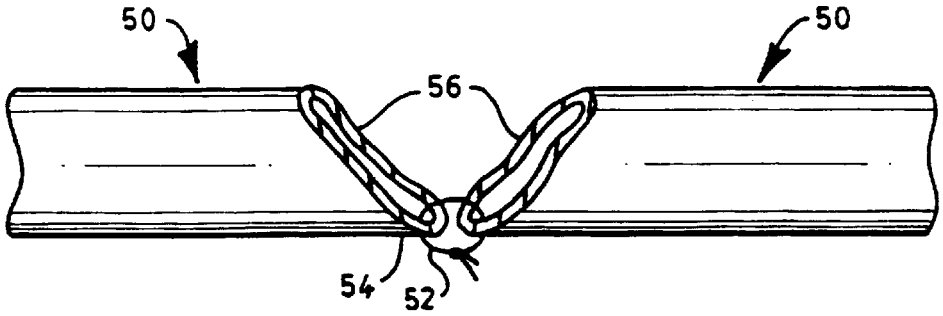
FIGS. 15–20 illustrates the remaining steps of the method of the present invention.

The method of the present invention can be used for both end-to-end anastomoses of tubular structures, as shown in FIG. 13, and end-to-side anastomoses of tubular structures, as shown in FIG. 14. The sequence of steps of the present invention for an end-to-end anastomosis is illustrated in the sequence of FIGS. 15–20. The method applies equally to an end-to-side anastomosis. In FIGS. 13 and 14, two tubular structures 50 are shown, their form irregular as a consequence of being severed and not being under internal pressure. As the first step in performing an anastomosis, shown in FIG. 15, an initial stitch 42 is placed to hold the two structures 50 together at one point. That point is generally on the back wall 54 of the anastomosis. The next step is to insert the device 10 into the openings 56 of the two structures 50. There are two preferred ways to insert the device. In the first, the device 10 is inserted completely into one of the tubular structures 50 and then slid back into the other tubular structure 50 until the device 10 is in the working position. In the second, the device 10 is folded at the bridge 16 and each arm 12 is inserted into the opening 56 of one of the tubular structures 50. After the bending pressure is removed, the device 10 straightens out into the working position, illustrated in phantom in FIGS. 16 and 17. In the working position, the depression 14 straddles the openings 56 of the tubular structures 50.

Figure 16:
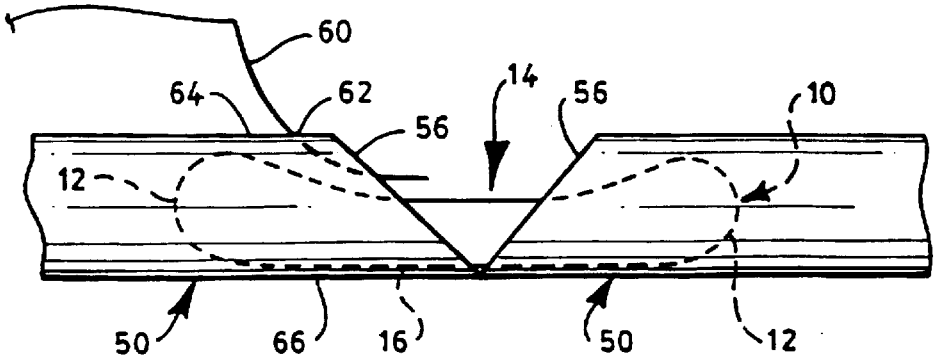
Figure 17:
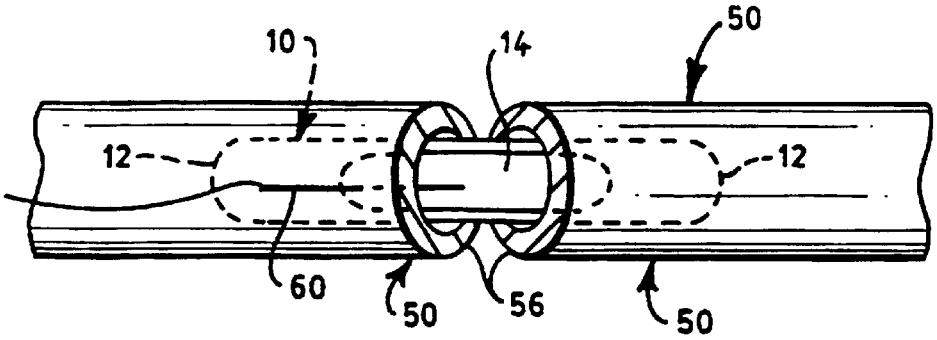
Figure 18:
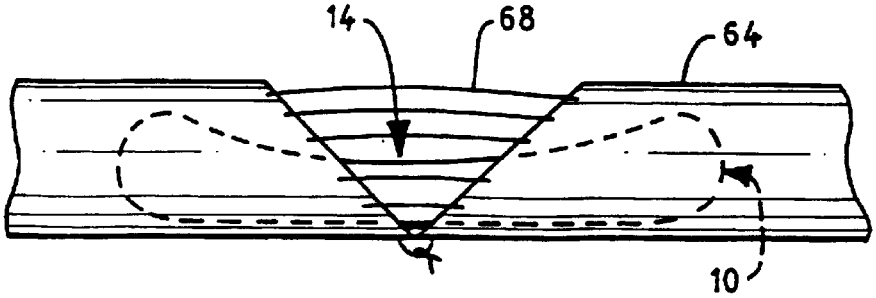

FIGS. 16 and 17 also show the needle 60 having pierced the wall 64 of one tubular structures 50 from outside to in. One arm 12 of the device 10 is situated adjacent to the insertion point 62 of the needle 60, exerting counter pressure to the needle thrust. The depression 14 allows room for the needle 60 to be passed perpendicular through the wall 64. The bridge 16 blocks the needle 60 from piercing the opposite wall 66. In FIG. 18, all of the sutures 68 are placed, either in a continuous suture, like a spiral, or as individual, separate sutures. As the sutures 68 are placed, the device 10 may be rotated so that the new suture 68 is centered in the depression 14. This provides maximum protection to the structure walls 64.

Figure 19:
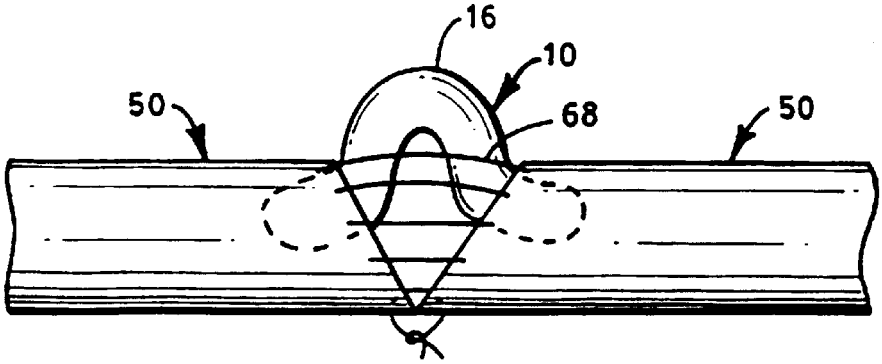
Figure 20:
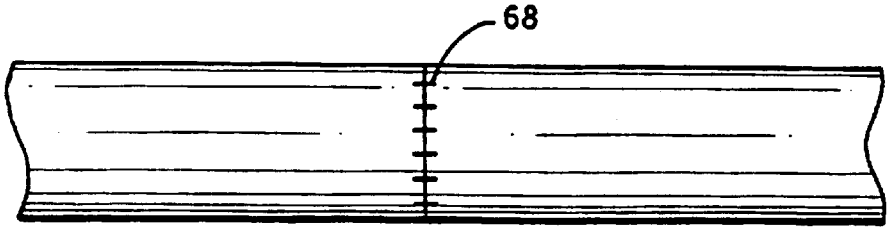

FIG. 19 illustrates the device 10 being flexed at the bridge 16 and removed from the tubular structures openings 56 prior to closure of the sutures 68. Alternatively, if the sutures 68 are loose enough, the device 10 is slid completely into one of the tubular structures 50, the tubular structures 50 are bent about the initial stitch 52, and the device 10 is slid out of the tubular structure opening 56. Finally, as shown in FIG. 20, the sutures 68 are tightened to complete the anastomosis.

While the above description relates to end-to-end anastomoses, the same principles apply to end-to-side anastomoses as well. In this instance, the two arms may be of differing configurations so as to fit into the differently-configured tubular openings to be joined. While examples have been cited relating to vessels of arterial, venous, and lymphatic nature, the joining of tubular structures other than vascular, for example, tubular structures of the biliary tree, urologic and reproductive systems, and the joining of synthetic grafts to tissues are within the scope of the invention.

Thus it has been shown and described a device and method for surgically joining tubular structures which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A device to aid in surgically joining a pair of tubular structures at openings thereof, said device [consisting of]*comprising*:

(a) a generally cylindrical body having a pair of opposed arms, a bridge between said arms, and a depression between said arms;

(b) said arms having free extremities that are adapted for insertion into said tubular structure openings;

(c) said depression being adapted to allow a suturing needle to pass through a wall of each of said tubular structures; and (d) said bridge being adapted to prevent trauma to said wall from said needle opposite where said needle passes through said wall.

2. The device of claim 1 wherein said extremities are convexly rounded.

3. The device of claim 1 wherein said extremities are tapered.

4. The device of claim 1 wherein said arms are substantially the same size.

5. The device of claim 1 wherein said arms are different sizes.

6. The device of claim 1 wherein said arms have a round cross-section.

7. The device of claim 1 wherein said arms have an oval cross-section.

8. The device of claim 1 wherein said arms have a C-shaped cross-section to permit said device to be compressible.

9. The device of claim 1 wherein one of said arms has a maximum cross-sectional area approximately that of the inside cross-sectional area of one of said tubular structures and the other of said arms has a maximum cross-sectional area approximately that of the inside cross-sectional area of the other of said tubular structures.

10. The device of claim 1 wherein said arms are solid.

11. The device of claim 1 wherein said arms include an axial bore.

12. The device of claim 1 wherein said bridge is substantially straight.

13. The device of claim 1 wherein said bridge is curved.

14. The device of claim 1 wherein said bridge is flexible.

15. The device of claim 1 wherein said depression is adapted to place counter pressure on said tubular structure wall when said needle is thrust through said wall in order to prevent said wall from collapsing against pressure from said needle thrust.

16. The device of claim 1 wherein said depression is configured to guide the path of said needle.

17. The device of claim 1 wherein said device is composed substantially of a biologically inert material.

18. The device of claim 1 wherein said device is composed substantially of a non-resorbable material.

19. The device of claim 1 wherein said device is composed substantially of a resorbable material.

20. The device of claim 1 wherein at least a portion of said device is radioopaque.

21. The device of claim 1 wherein at least a portion of said device is magnetized.

22. The device of claim 1 wherein at least a portion of said device includes at least one material selected from the group consisting of an anticoagulant, an antibiotic, an antiseptic, a lubricant, and a vascular spasm inhibitor.

23. The device of claim 1 wherein said device [is] includes a structure for grasping.

24. A device to aid in surgically joining a pair of tubular structures at openings thereof, said device [consisting of]*comprising*:

(a) a generally cylindrical body having a pair of opposed arms, a bridge between said arms, and a depression between said arms;

(b) said arms having free extremities that are adapted for insertion into said tubular structure openings, one of said arms having a maximum cross-sectional area approximately that of the inside cross-sectional area of one of said tubular structures and the other of said arms having a maximum cross-sectional area approximately that of the inside cross-sectional area of the other of said tubular structures;

(c) said depression being adapted to allow a suturing needle to pass through a wall of each of said tubular structures; and (d) said bridge being flexible and substantially straight and being adapted to prevent trauma to said wall from said needle opposite where said needle passes through said wall.

25. The device of claim 24 wherein said extremities are convexly rounded.

26. The device of claim 24 wherein said extremities are tapered.

27. The device of claim 24 wherein said arms are substantially the same size.

28. The device of claim 24 wherein said arms are different sizes.

29. The device of claim 24 wherein said arms have a round cross-section.

30. The device of claim 24 wherein said arms have an oval cross-section.

31. The device of claim 24 wherein said arms have a C-shaped cross-section to permit said device to be compressible.

32. The device of claim 24 wherein said arms are solid.

33. The device of claim 24 wherein said arms include an axial bore.

34. The device of claim 24 wherein said depression is adapted to place counter pressure on said tubular structure wall when said needle is thrust through said wall in order to prevent said wall from collapsing against pressure from said needle thrust.

35. The device of claim 24 wherein said depression is configured to guide the path of said needle.

36. The device of claim 24 wherein at least a portion of said device includes at least one material selected from the group consisting of an anticoagulant, an antibiotic, an antiseptic, a lubricant, and a vascular spasm inhibitor.

37. The device of claim 24 wherein said device [is] includes a structure for grasping.

38. A method for surgically joining a pair of tubular structures at openings thereof, said method comprising the steps of:

(a) providing a device with a generally cylindrical body having a pair of opposed arms, a bridge between said arms, and a depression between said arms, said arms having free extremities that are adapted for insertion into said tubular structure openings, said depression being adapted to allow a suturing needle to pass through a wall of each of said tubular structures, and said bridge being adapted to prevent trauma to said wall from said needle opposite where said needle passes through said wall;

(b) placing a single suture at said tubular structure openings to hold said tubular structures together at a single point;

(c) inserting said device arm extremities into said tubular structure openings;

(d) positioning said device in a working position such that said depression straddles said tubular structure openings;

(e) introducing sutures into said tubular structure walls at suture positions adjacent to said depression for permitting the suturing needle to traverse through said walls;

(f) removing said device; and (g) tightening said sutures.

39. The method of claim 38 wherein inserting and positioning said device includes inserting said device substantially fully into a first of said tubular structures, aligning said openings, and sliding said device into a second of said tubular structures until said device is in said working position.

40. The method of claim 38 wherein inserting said device includes the use of a grasping tool.

41. The method of claim 38 wherein said device is rotated prior to introducing each of said sutures such that said depression is aligned with said suture position.

42. The method of claim 38 wherein said bridge is flexible and removing said device includes bending said device at said bridge such that said bridge extends outwardly through said sutures.

43. The method of claim 38 wherein removing said device includes the use of a grasping tool.

* * * * *